United States Patent [19]

Gsell et al.

[11] 4,265,897

[45] May 5, 1981

[54] N-N-DIMETHYL-1-(1'-METHYL-2'-METHOXYETHYL)-1,2,4-TRIAZOLYLCARBAMATES

[75] Inventors: Laurenz Gsell, Basel; Peter Ackermann, Reinach; Rudolf Wehrli, Rheinfelden, all of Switzerland

[73] Assignee: Ciba-Geigy Corporation, Ardsley, N.Y.

[21] Appl. No.: 91,631

[22] Filed: Nov. 5, 1979

[30] Foreign Application Priority Data

Nov. 14, 1978 [CH] Switzerland .................. 11690/78

[51] Int. Cl.³ .................. A01N 43/64; C07D 249/12
[52] U.S. Cl. .................. 424/269; 548/264; 548/265
[58] Field of Search .................. 548/262, 264, 265; 424/269

[56] References Cited

U.S. PATENT DOCUMENTS

| | | | |
|---|---|---|---|
| 3,794,661 | 2/1974 | Boehner et al. | 548/265 |
| 3,809,701 | 5/1974 | Dawes et al. | 548/265 |
| 3,862,125 | 1/1975 | Hoffmann et al. | 548/264 |
| 4,172,080 | 10/1979 | Dawes et al. | 424/200 |

FOREIGN PATENT DOCUMENTS

| | | | |
|---|---|---|---|
| 2651556 | 5/1977 | Fed. Rep. of Germany | 424/200 |
| 2739084 | 3/1978 | Fed. Rep. of Germany | 424/200 |
| 549942 | 4/1974 | Switzerland | 424/269 |
| 573206 | 3/1976 | Switzerland | 424/269 |

*Primary Examiner*—Alton D. Rollins
*Attorney, Agent, or Firm*—Frederick H. Rabin

[57] ABSTRACT

Triazolylcarbamates of the formula

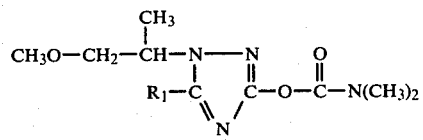

wherein $R_1$ is hydrogen, chlorine, $C_1$-$C_4$-alkyl, $C_1$-$C_4$-alkoxy or $C_1$-$C_4$-alkylthio, processes for producing them, and their use for combating insect pests.

8 Claims, No Drawings

N-N-DIMETHYL-1-(1'-METHYL-2'-METHOXYETHYL)-1,2,4-TRIAZOLYLCARBAMATES

The present invention relates to triazolylcarbamate derivatives, to processes for producing them, and to their use for combating insect pests.

The triazolylcarbamate derivatives have the following formula

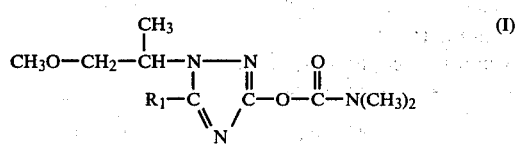

wherein $R_1$ is hydrogen, chlorine, $C_1$–$C_4$-alkyl, $C_1$–$C_4$-alkoxy or $C_1$–$C_4$-alkylthio.

The alkyl groups denoted by $R_1$ can be straight-chain or branched-chain. Examples of such groups are, inter alia: methyl, methoxy, methylthio, ethyl, ethoxy, ethylthio, n-propyl, n-propoxy, n-propylthio, n-, i-, sec- or tert-butyl, n-butoxy, i-propyl, n-butylthio, isopropoxy and iso-propylthio.

The compounds of the formula I can be produced by methods known per se, for example as follows:

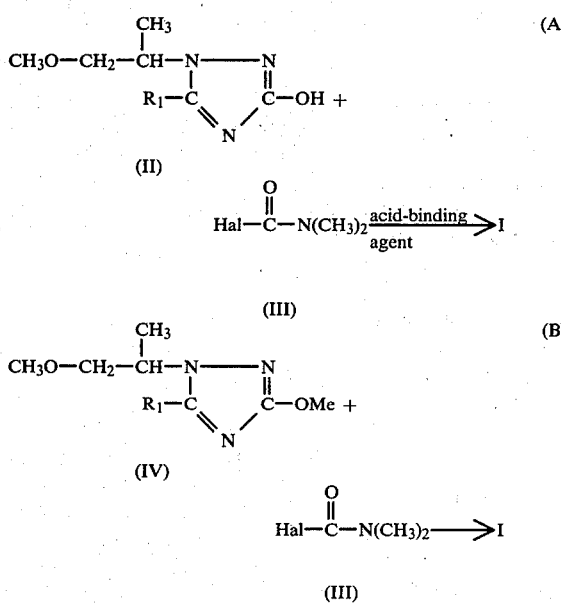

In the formulae II to IV, the symbol $R_1$ has the meaning defined under the formula I, "Hal" is halogen, preferably chlorine or bromine, and "Me" denotes a metal, particularly an alkali metal, ammonium or trialkylammonium.

Suitable acid-binding agents are for example the following bases: tertiary amines, such as triethylamine, dimethylaniline or pyridine; and inorganic bases, such as hydroxides and carbonates of alkali metals and alkaline-earth metals, preferably sodium and potassium carbonate.

The processes A and B are performd at a reaction temperature of 0°–120° C., preferably at 20°–80° C., under normal pressure, and in solvents or diluents. Suitable solvents or diluents are for example: ethers and ethereal compounds, such as diethyl ether, dipropyl ether, dioxane, dimethoxyethane and tetrahydrofuran; amides, such as N,N-dialkylated carboxylic acid amides; aliphatic, aromatic as well as halogenated hydrocarbons, particularly benzene, toluene, xylenes, chloroform and chlorobenzene; nitriles, such as acetonitrile; dimethyl sulfoxide; and ketones, such as acetone or methyl ethyl ketone; and water.

The compounds of the formula I are suitable for combating various animal and plant pests. The compounds thus have for example nematicidal, fungicidal and bactericidal activity.

The compounds of the formula I are especially suitable for combating insects, phytopathogenic mites and ticks, for example of the orders: Lepidoptera, Coleoptera, Homoptera, Heteroptera, Diptera, Acarina, Thysanoptera, Orthoptera, Anoplura, Siphonaptera, Mallophaga, Thysanura, Isoptera, Psocoptera and Hymenoptera. The compounds of the formula I are suitable in particular for combating insects that damage plants, especially insects that damage plants by eating, in crops of ornamental plants and useful plants, particularly in cotton crops (for example against *Spodoptera littoralis* and *Heliothis virescens*), and in crops of vegetables (for example against *Leptinotarsa decemlineata* and *Myzus persicae*). Active substances of the formula I have a very favourable action also against flies, such as *Musca domestica*, and against mosquito larvae.

The acaricidal and insecticidal action can be substantially broadened and adapted to suit given circumstances by the addition of other insecticides and/or acaricides. Suitable additives are for example: organic phosphorus compounds; nitrophenols and derivatives thereof; formamidines; ureas; pyrethrin-like compounds; as well as other carbamates and chlorinated hydrocarbons.

Compounds of the formula I are combined particularly advantageously also with substances which have a hydrotropic effect. Examples of compounds of this kind are, inter alia: piperonylbutoxide, propynyl ethers, propynyl oximes, propynyl carbamates and propynyl phosphonates, 2-(3,4-methylenedioxyphenoxy)-3,6,9-trioxaundecane (Sesamex or Sesoxane), S,S,S-tributylphosphorotrithioates and 1,2-methylenedioxy-4-(2-(octylsulfonyl)-propyl)-benzene.

Compounds of the formula I can be used on their own or together with suitable carriers and/or additives. Suitable carriers and additives can be solid or liquid and they correspond to the substances common in formulation practice, such as natural or regenerated substances, solvents, dispersing agents, wetting agents, adhesives, thickeners, binders and/or fertilisers.

The compositions according to the invention are produced in a manner known per se by the intimate mixing and/or grinding of the active substances of the formula I with suitable carriers, optionally with the addition of dispersing agents or solvents which are inert to the active substances. The active substances can be obtained and used in the following forms:

solid preparations dusts, scattering agents, granules (coated granules, impregnated granules and homogeneous granules);

liquid preparations (a) water-dispersible concentrates of active substance: wettable powders, pastes or emulsions;
(b) solutions.

The content of active substance in the compositions described above is between 0.1 and 95%; it is to be mentioned in this respect that with application from an aeroplane, or from other suitable devices, concentrations of up to 99.5% or even the pure active substance can be used.

The active substances of the formula I can be formulated for example as follows (parts are by weight).

Dusts

The following substances are used to produce (a) a 5% dust and (b) a 2% dust:

(a)

5 parts of active substance, and
95 parts of talcum; and (b)

2 parts of active substance,
1 part of highly dispersed silicic acid, and
97 parts of talcum.

The active substance is mixed and ground with the carriers.

Granulate

The following ingredients are used to produce a 5% granulate:
5 parts of active substance,
0.25 part of epoxidised vegetable oil,
0.25 part of cetyl polyglycol ether,
3.50 parts of polyethylene glycol, and
91 parts of kaolin (particle size 0.3–0.8 mm).

The active substance is mixed with epichlorohydrin and the mixture is dissolved in 6 parts of acetone; the polyethylene glycol and cetyl polyglycol ether are then added. The solution thus obtained is sprayed onto kaolin, and the acetone is subsequently evaporated off in vacuo.

Wettable powders

The following constituents are used to produce (a) a 40% wettable powder, (b) and (c) a 25% wettable powder and (d) a 10% wettable powder:

(a)

40 parts of active substance,
5 parts of sodium lignin sulfonate,
1 part of sodium dibutyl-naphthalene sulfonate, and
54 parts of silicic acid;

(b)

25 parts of active substance,
4.5 parts of calcium lignin sulfonate,
1.9 parts of Champagne chalk/hydroxyethyl cellulose mixture (1:1),
1.5 parts of sodium dibutyl-naphthalene sulfonate,
19.5 parts of silicic acid,
19.5 parts of Champagne chalk, and
28.1 parts of kaolin;

(c)

25 parts of active substance,
2.5 parts of isooctylphenoxy-polyoxyethylene-ethanol,
1.7 parts of Champagne chalk/hydroxyethyl cellulose mixture (1:1),
8.3 parts of sodium aluminium silicate,
16.5 parts of kieselguhr, and
46 parts of kaolin; and (d)

10 parts of active substance,
3 parts of a mixture of the sodium salts of saturated fatty alcohol sulfates,
5 parts of naphthalenesulfonic acid/formaldehyde condensate, and
82 parts of kaolin.

The active substance is intimately mixed in suitable mixers with the additives, and the mixture is then ground in the appropriate mills and rollers to obtain wettable powders which can be diluted with water to give suspensions of the concentration desired.

Emulsifiable concentrates

The following substances are used to produce (a) a 10% emulsifiable concentrate, (b) a 25% emulsifiable concentrate and (c) a 50% emulsifiable concentrate:

(a)

10 parts of active substance,
3.4 parts of epoxidised vegetable oil,
3.4 parts of a combination emulsifier consisting of fatty alcohol polyglycol ether and alkylarylsulfonate calcium salt,
40 parts of dimethylformamide, and
43.2 parts of xylene;

(b)

25 parts of active substance,
2.5 parts of epoxidised vegetable oil,
10 parts of alkylarylsulfonate/fatty alcohol polyglycol ether mixture,
5 parts of dimethylformamide, and
57.5 parts of xylene; and (c)

50 parts of active substance,
4.2 parts of tributylphenol-polyglycol ether,
5.8 parts of calcium-dodecylbenzenesulfonate,
20 parts of cyclohexanone, and
20 parts of xylene.

Emulsions of the required concentration can be prepared from these concentrates by dilution with water.

Sprays

The following constituents are used to produce (a) a 5% spray and (b) a 95% spray:

(a)

5 parts of active substance,
1 part of epoxidised vegetable oil, and
94 parts of ligroin (boiling limites 160°–190° C.); and (b)

95 parts of active substance, and
5 parts of epichlorohydrin.

The invention is further illustrated by the Examples which follow.

EXAMPLE 1

Production of N,N-dimethyl-1-(1-methyl-2-methoxyethyl)-5-chloro-1,2,4-triazolyl carbamate 0.1 mol of the compound of the formula $$CH_3O-CH_2-\underset{\underset{Cl-C}{|}}{\overset{\overset{CH_3}{|}}{CH}}-\underset{\underset{\diagdown N \diagup}{}}{N}\overset{\overset{}{\phantom{x}}}{\underset{}{\phantom{x}}}\overset{\parallel}{C}-OH$$

with 0.1 mol of anhydrous pulverised potassium carbonate in 500 ml of methyl ethyl ketone is heated at 80° C. for four hours. After cooling, there is added at room temperature 0.1 mol of dimethylcarbamoyl chloride, and the reaction mixture is subsequently stirred at 40° C. for 12 hours. After filtration of the salts and removal of the solvent, recrystallisation of the crude product yields the compound of the formula $$CH_3OCH_2-\underset{\underset{\underset{Cl-C}{|}}{\underset{|}{N}}}{\overset{\overset{CH_3}{|}}{CH}}\overset{\overset{}{\phantom{x}}-N}{\underset{\diagdown N \diagup}{}}\overset{O\phantom{xxx}O}{\overset{\parallel\phantom{xxx}\parallel}{C-O-C-N(CH_3)_2}}$$

having a melting point of 82°–84° C.

The following compounds are produced in an analogous manner:

$$CH_3-O-CH_2-\underset{\underset{\underset{R_1-C}{|}}{\underset{|}{N}}}{\overset{\overset{CH_3}{|}}{CH}}\overset{-N}{\underset{\diagdown N \diagup}{}}\overset{O\phantom{xxx}O}{\overset{\parallel\phantom{xxx}\parallel}{C-O-C-N(CH_3)_2}}$$

| $R_1$ | |
|---|---|
| —CH$_3$ | m.p.: 105–106° C. |
| H | m.p.: 54–55° C. |
| —SCH$_3$ | $n_D^{20°} = 1.5110$ |
| —SC$_2$H$_5$ | m.p.: 46–48° C. |
| —SC$_3$H$_7$(i) | m.p.: 64–67° C. |
| —OCH$_3$ | $n_D^{20°} = 1.4742$ |
| —OC$_3$H$_7$(i) | $n_D^{20°} = 1.4678$ |
| —OC$_2$H$_3$ | $n_D^{20°} = 1.4708$ |

EXAMPLE 2

(A) Insecticidal stomach-poison action

Cotton plants were sprayed with a 0.05% aqueous emulsion of the active substance (obtained from a 10% emulsifiable concentrate).

After drying of the coating, larvae of *Spodoptera littoralis* in the L$_3$ stage and of *Heliothis virescens* in the L$_3$ stage were settled onto the cotton plants. The test was carried out at 24° C. with 60% relative humidity.

Compounds according to Example 1 exhibited in the above test a good insecticidal stomach-poison action against larvae of *Spodoptera littoralis* and *Heliothis virescens*, (B) Systemic insecticidal action In order to determine the systemic action, rooted bean plants (*Vicia faba*) were placed into a 0.01% aqueous solution of the active substance (obtained from a 10% emulsifiable concentrate). After 24 hours, bean aphids (*Aphis fabae*) were placed onto the parts of the plants which had been above the soil. By means of a special device, the bean aphids were protected from the effects of contact and of gas. The test was carried out at 24° C. with 70% relative humidity.

Compounds according to Example 1 exhibited in the above test a systemic insecticidal action against *Aphis fabae*.

EXAMPLE 3

Acaricidal action

*Phaseolus vulgaris* plants were infested, 12 hours before the test for acaricidal action, with an infested piece of leaf from a mass culture of *Tetranychus urticae*. The transferred mobile stages were sprayed with the emulsified test preparations from a chromatography-sprayer in a manner ensuring no overflow of the spray liquor. An assessment was made after 2 and 7 days, respectively, by examination under a binocular microscope, of the living and of the dead larvae, adults and eggs, and the results were expressed as percentages. The treated plants were kept during the holding time in greenhouse compartments at 25° C.

Compounds according to Example 1 exhibited in the above test a good action against adults, larvae and eggs of *Tetranychus urticae*.

EXAMPLE 4

Action against soil nematodes

In order to test their action against soil nematodes, the active substances were added to soil infested with root-gall nematodes (*Meliodogyne arenaria*), and intimately mixed with the soil. In one test series, tomato seedlings were planted immediately after preparation of the soil in the manner described, and in the other test series tomatoes were sown after a waiting time of 8 days. An assessment of the nematocidal action was made by counting the galls present on the roots 28 days after planting and sowing, respectively.

Active substances according to Example 1 exhibitied in this test a good action against *Meloidogyne arenaria*.

EXAMPLE 5

Action against ticks (A) *Rhipicephalus bursa*

For each concentration, 5 adult ticks and 50 tick larvae, respectively, were counted into a small glass test tube, and immersed for 1 to 2 minutes in 2 ml of an aqueous emulsion from a dilution series of 100, 10, 1 and 0.1 ppm of test substance. The tubes were then sealed with a standardised cotton plug, and inverted so that the active-substance emulsion could be absorbed by the cotton wool.

The evaluation in the case of the adults was made after 2 weeks and in the case of the larvae after 2 days. There were two repeats for each test.

(B) *Boophilus microplus* (larvae)

With a dilution series analogous to that of Test A, tests were carried out with 20 sensitive larvae and OP-resistant larvae, respectively (resistance is with respect to diazinon compatibility).

Compounds according to Example 1 were effective in these tests against adults and larvae of *Rhipicephalus bursa* and against sensitive and OP-resistant larvae, respectively, of *Boophilus microplus*.

EXAMPLE 6

Action against *Erysiphe graminis* on *Hordeum vulgare*

Barley plants about 8 cm in height were sprayed with a spray liquor (0.05% of active substance) produced from wettable powder of the active substance. The treated plants were dusted after 48 hours with conidia of the fungus. The infested barley plants were placed in a greenhouse at about 22° C., and the fungus infection was assessed after 10 days.

Compounds according to Example 1 were effective in this test against *Erysiphe graminis*.

What is claimed is:

1. A compound of the formula

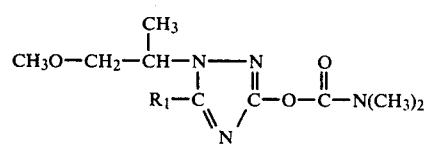

wherein $R_1$ is hydrogen, chlorine, $C_1$-$C_4$-alkyl, $C_1$-$C_4$-alkoxy or $C_1$-$C_4$-alkylthio.

2. The compound according to claim 1 of the formula

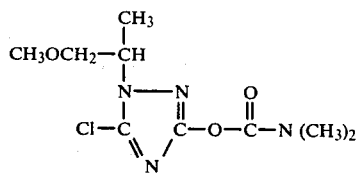

3. The compound according to claim 1 of the formula

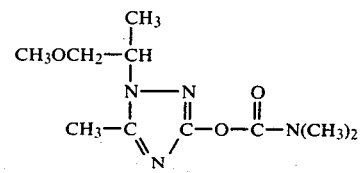

4. The compound according to claim 1 of the formula

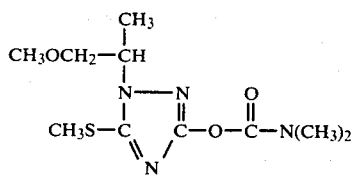

5. The compound according to claim 1 of the formula

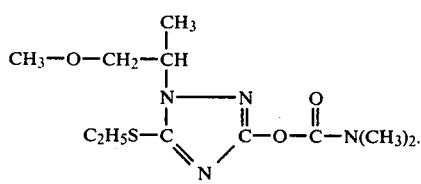

6. The compound according to claim 1 of the formula

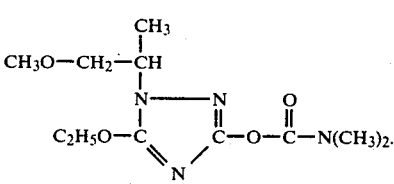

7. An insecticidal and acaricidal composition comprising a compound according to claim 1 as active ingredient, and a carrier.

8. A method for combatting insects and acarids which comprises applying thereto an insecticidally or acaricidally effective amount of a compound according to claim 1.

* * * * *